(12) United States Patent
Severa

(10) Patent No.: US 7,086,796 B2
(45) Date of Patent: Aug. 8, 2006

(54) DISPENSING DEVICE

(75) Inventor: Raymond J. Severa, Westlake, OH (US)

(73) Assignee: Bonne Bell, Inc., Lakewood, OH (US)

( * ) Notice: Subject to any disclaimer, the term of this patent is extended or adjusted under 35 U.S.C. 154(b) by 412 days.

(21) Appl. No.: 10/632,346

(22) Filed: Aug. 1, 2003

(65) Prior Publication Data

US 2005/0025558 A1 Feb. 3, 2005

(51) Int. Cl.
*B43K 5/06* (2006.01)
*B05C 11/00* (2006.01)

(52) U.S. Cl. .................. 401/179; 401/182; 401/266

(58) Field of Classification Search ............. 401/65, 401/66, 176, 177, 179, 180, 182, 265, 266, 401/278, 279, 272; 222/80, 391, 326
See application file for complete search history.

(56) References Cited

U.S. PATENT DOCUMENTS

| | | |
|---|---|---|
| 1,546,516 A | 7/1925 | Smith |
| 1,668,511 A | 5/1928 | McLaughlin |
| D118,872 S | 2/1940 | Vassos |
| D143,508 S | 1/1946 | Reynolds |
| D144,358 S | 4/1946 | Fish et al. |
| D147,107 S | 7/1947 | Breitenstein |
| D153,713 S | 5/1949 | Lohr et al. |
| D157,471 S | 2/1950 | Doux |
| D159,978 S | 9/1950 | Green et al. |
| 2,528,839 A | 11/1950 | Mason |
| D161,426 S | 1/1951 | Covey et al. |
| 2,541,949 A * | 2/1951 | Thacker et al. ............. 401/179 |
| 2,590,329 A | 3/1952 | Kromray |
| 2,609,093 A | 9/1952 | Lynn |
| 2,695,028 A | 11/1954 | Dulberg |
| 2,718,299 A | 9/1955 | Altwater et al. |
| D176,364 S | 12/1955 | Manville |
| D176,372 S | 12/1955 | Noyack |
| 2,771,858 A | 11/1956 | Cribbs et al. |
| D180,964 S | 9/1957 | Slater |
| D185,319 S | 5/1959 | Schlumberger |
| D185,337 S | 5/1959 | Wolff |
| 3,275,132 A | 9/1966 | Hultgren |
| 3,338,397 A | 8/1967 | Noyack et al. |
| 3,351,074 A | 11/1967 | Aston |
| 3,358,699 A | 12/1967 | Bau |
| 3,378,176 A | 4/1968 | Snyder |
| 3,728,034 A | 4/1973 | Winter |
| 3,902,814 A | 9/1975 | Cardia |
| 3,989,392 A | 11/1976 | Seidler |
| 4,506,810 A | 3/1985 | Goncalves |
| 4,659,327 A | 4/1987 | Bennett et al. |
| 4,699,161 A | 10/1987 | Smith et al. |
| 4,766,272 A * | 8/1988 | Guzzon ................ 200/302.2 |
| 4,892,427 A | 1/1990 | Ford |
| D306,458 S | 3/1990 | Lecce |
| D310,100 S | 8/1990 | Yubisui |
| D312,478 S | 11/1990 | Lecce |
| 5,011,317 A | 4/1991 | Gueret |
| D321,009 S | 10/1991 | Yubisui |
| D321,719 S | 11/1991 | Nitta |

(Continued)

FOREIGN PATENT DOCUMENTS

FR 536131 4/1922

*Primary Examiner*—David J. Walczak
(74) *Attorney, Agent, or Firm*—Hudak, Shunk & Farine Co. LPA

(57) ABSTRACT

A dispensing device for substances including personal care, cosmetics, and medicinal substances dispenses a metered amount by actuation of a push button which indirectly contacts an advancable shaft, thereby driving a piston to push the substance from a reservoir into an applicator. The device can be operated in one hand of a person and is devoid of any twist or rotation mechanism.

38 Claims, 3 Drawing Sheets

U.S. PATENT DOCUMENTS

| | | | |
|---|---|---|---|
| D327,912 S | 7/1992 | Tsai | |
| D329,660 S | 9/1992 | Yamanaka | |
| D329,873 S | 9/1992 | Tu | |
| D360,223 S | 7/1995 | Lamber | |
| D374,251 S | 10/1996 | Briggl | |
| D374,460 S | 10/1996 | Young | |
| D375,524 S | 11/1996 | Takahashi | |
| D377,194 S | 1/1997 | Young | |
| D389,864 S | 1/1998 | Jones et al. | |
| 5,807,346 A | 9/1998 | Frezza | |
| D406,277 S | 3/1999 | Lecce | |
| 5,944,435 A | 8/1999 | Chai | |
| D416,645 S | 11/1999 | Spudeno | |
| D416,940 S | 11/1999 | Ito | |
| D420,767 S | 2/2000 | Coates et al. | |
| D421,156 S | 2/2000 | Coates et al. | |
| D421,770 S | 3/2000 | Saski | |
| D422,748 S | 4/2000 | Lang | |
| D426,263 S | 6/2000 | Sekine et al. | |
| D426,573 S | 6/2000 | Sekine et al. | |
| D436,624 S | 1/2001 | Zier | |
| D443,303 S | 6/2001 | Ashe | |
| D452,272 S | 12/2001 | Bonnamour | |
| D452,527 S | 12/2001 | Maki et al. | |
| D454,366 S | 3/2002 | Qiu | |
| D454,586 S | 3/2002 | Qiu | |
| D454,587 S | 3/2002 | Qiu | |
| 6,394,270 B1 | 5/2002 | Liu | |
| D458,456 S | 6/2002 | Dragan et al. | |
| D459,393 S | 6/2002 | Verhaeghe | |
| D463,489 S | 9/2002 | Yoon | |
| D463,491 S | 9/2002 | Hwang | |
| D465,521 S | 11/2002 | Qiu | |
| 6,474,891 B1 | 11/2002 | Liu | |
| 6,746,170 B1 * | 6/2004 | Delage | 401/266 |
| 2002/0067947 A1 | 6/2002 | Liu | |
| 2002/0164193 A1 | 11/2002 | Brown | |

\* cited by examiner

FIG. 3
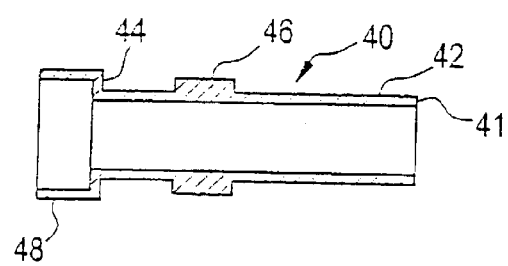
FIG. 4
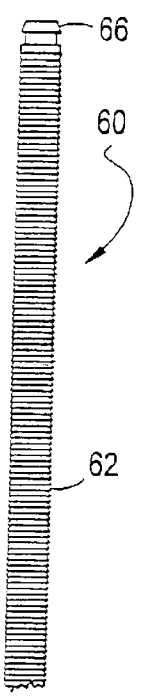
FIG. 5
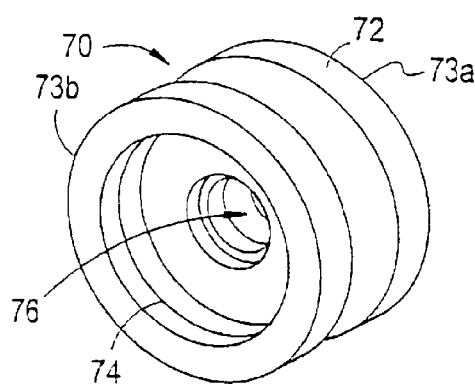
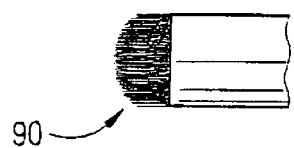
FIG. 6A
FIG. 6
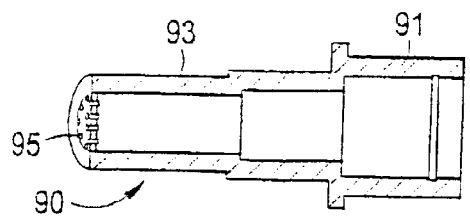
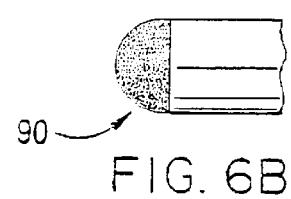
FIG. 6B

DISPENSING DEVICE

BACKGROUND OF THE INVENTION

1. Field of the Invention

The present invention is directed to a dispensing device, and in particular to a device which is operable by a push button action so as to dispense a predetermined amount of a desired substance such as a cosmetic, lotion, cream, or medicinal. More specifically, the present invention relates to dispensing metered amounts of the substance through the utilization of a push cap which indirectly drives a shaft connected to a piston slidably engaging a substance-containing reservoir to dispense the substance through an applicator. A tandem set of ratchet springs in conjunction with a constant pitched shaft provides a metered amount of the substance to the applicator when a push button is pressed.

2. Description of the Related Art

Numerous devices exist for the dispensing of cosmetic substances from a holder. Such devices usually consist of an outer tubular shell or housing, a cap and a moveable mechanism for displacement of the cosmetic substance. The mechanisms are conventionally based on a twist or rotation of a tubular housing to dispense the product. Such a mechanism is taught in U.S. Pat. No. 6,474,891 which discloses a make-up pen which dispenses a cosmetic lotion/cream by rotating a rotational cap.

These rotational mechanisms have the inherent drawback, however, of requiring the use of both hands of the person applying the cosmetic, one to hold the housing and the other to impart rotation of the mechanism. The devices further have the drawback of requiring the user to rotate the device a plurality of times in order to obtain the desired or required amount of product to be dispensed.

Other devices relate to mechanical pencils in which the lead is generally advanced by pressing a shaft which at one end projects from the top end of the pencil and at the other end is connected to a toothed shaft which advances the lead. Such a mechanism is set forth in U.S. Pat. No. 2,771,858 to Cribbs which relates to a mechanical pencil having a barrel in which is axially shiftable a push rod terminating in a button projecting beyond one end of the barrel, the push rod being operably engaged by means of a pawl with a rack, and the barrel carrying a holding pawl which prevents retrograde movement of the rack. On each depression of the push button, the rack is advanced a predetermined number of steps and carried by the rack is a lead which is correspondingly advanced on each advancing movement of the rack. Associated with the rack is a means for rotating the same at the option of a user, through a sufficient number of degrees to disengage the same from the pawls, and when the rack is so rotated, a spring means associated therewith returns it to its original position, so that a new lead can be inserted.

Another device relates to mechanical pens or cosmetic dispensers such as lipstick wherein a wheel is utilized to drive and advance a cylinder or sleeve containing lipstick and the like. Such a device is set forth in U.S. Pat. No. 6,394,270 wherein a lipstick case includes a tubular housing, a connecting sleeve fitted within the tubular housing and having an upper end extending out of the tubular housing, a cap engageable with an upper end of the connecting sleeve, a core movably mounted within the connecting sleeve and having a chamber for receiving a lipstick, the core having a downwardly extending member, a supporting bracket disposed within the tubular housing and provided with two vertical members, a hand wheel rotatably arranged between the two vertical members and formed with two gears at two sides thereof, and a toothed rack fixedly mounted on an inner side of the downwardly extending member of the core and meshed with one of the gears of the hand wheel. Such wheel-type dispensers can inadvertently advance the contents of the container resulting in contamination of a hand bag or the like, unless a safety lock is utilized.

It would therefore, be desirable to provide a dispensing device which can be actuated by a push button action which through indirect contact with a shaft advances the same to provide a predetermined amount of a desired substance.

SUMMARY OF THE INVENTION

The present invention provides a dispensing device. The dispensing device can be actuated by depression of a slidable push button which, through a housing having a peripheral contact with an advancable shaft, operatively dispenses a predetermined amount of a desired substance. The shaft has a piston at one end located within a reservoir to drive forward the substance into an applicator whereby it is dispensed. The use of a slidable push button forms an aesthetically pleasing design and due to the indirect contact, there is no contact with the top of the shaft.

BRIEF DESCRIPTION OF THE DRAWINGS

FIG. 3 is a cross section of the plunger of the present invention.

FIG. 4 is an enlarged sectional view of the center toothed shaft of the present invention.

FIG. 5 is an exploded view of the piston head of the dispensing device of the present invention.

FIG. 6 is a sectional view of the applicator.

FIG. 6A is a perspective view of the applicator shown in FIG. 6 including a brush.

FIG. 6B is a perspective view of the applicator shown in FIG. 6 including a sponge.

DESCRIPTION OF THE INVENTION

Figure 1:
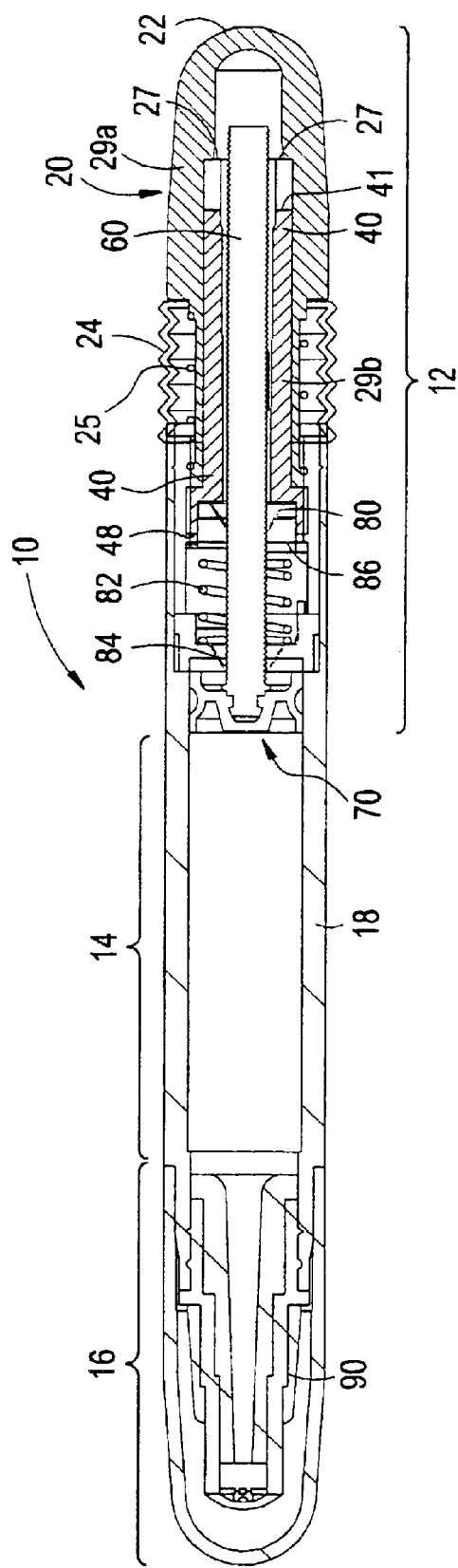
FIG. 1 is a cross sectional side view of a dispensing device according to the present invention.

In an embodiment of the present invention as shown in FIG. 1, there is illustrated a dispensing device 10. Throughout this description, for ease of referral; any item or component located on the left side of FIG. 1 or with respect to any component located to the left of an element of the dispensing device will be indicated as being a lower component. Similarly, components located to the right of any indicated element will be indicated as an upper component.

Dispensing device 10 has an outer cylinder 18 preferably of an essentially consistent diameter along a major length of the device and includes an upper portion 12 having housing 20, a center reservoir portion 14 and a lower cap portion 16 having applicator 90 therein. The lower cap portion 16, as well as the upper portion 12, at the extremities thereof, preferably taper inwardly to form slightly elongated and rounded ends. Important aspects of the present invention are that upper housing 20 is slidable in a forward or downward longitudinal direction and that the upper end thereof forms an integral push button 22 which does not directly contact the upper end or terminal portion of advancable center toothed shaft 60. In other words, as will be more fully discussed hereinbelow, while a downward push on push button 22 will advance flow of a substance through the applicator, push button 22 is free of any contact with the top portion of shaft 60. The top portion of the shaft can be defined as the generally flat surface thereof or the upper approximate 5% or 10% of its total length. Located below push button 22, is an accordion-pleated flexible plastic sleeve portion 24 which is capable of expanding and contracting as the push button is pressed and released.

The various components of the dispensing device can be made from rubber, plastic, or less desirably metal. Preferably, the various components or parts are made of plastic. For example, housing 20 containing push button 22 can be made of one or more semi-rigid plastics which have some flexibility such as polybutylene, polyesters such as polyethylene terephthalate, various grades of polyethylene such as low or high density polyethylene, ethylene-ethyl acrylate, ethylene-vinyl acetate, polypropylene and the like with polypropylene being preferred for its chemical resistance, flexibility and durability. The flexible pleated sleeve portion 24 is naturally made of one or more soft, flexible plastics such as silicone rubber, polypropylene, low density and ultra-low density polyethylene, and polybutylene with silicone being preferred. Reservoir portion 14, and lower cap portion 16 are desirably made of one or more semi-flexible materials such as polyester, polyethylene, polybutylene, ethylene-ethyl acrylate, or ethylene-vinyl acetate, and the like with polypropylene being preferred. Applicator 90 is made of a flexible material such as a polyester elastomer. The center toothed shaft 60 will generally be made from a metal such as stainless steel, aluminum, or brass, with aluminum being preferred due to its durability and machinability.

Figure 2:
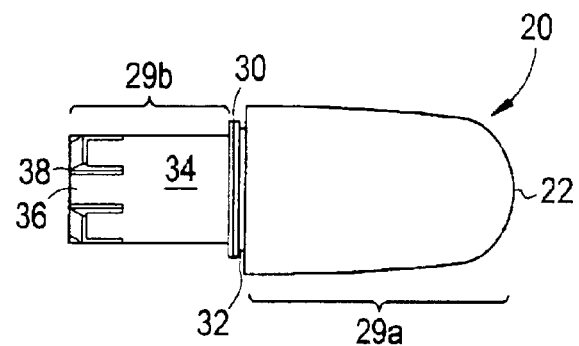
FIG. 2 is a plan view of the outside of the upper housing of the dispensing device.
Figure 2A:
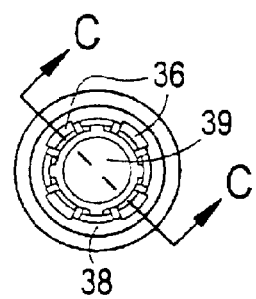
FIG. 2A is cross-sectional view of the bottom segment of the upper housing.
Figure 2B:
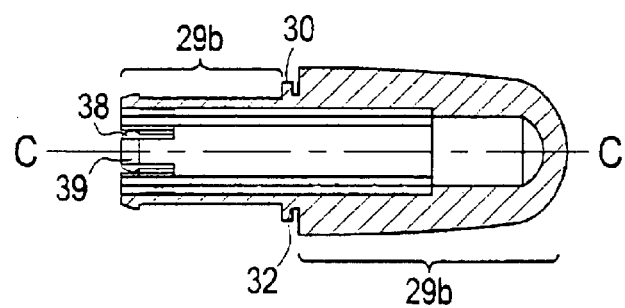
FIG. 2B is a cross section of FIG. 2A taken through line C—C.

In FIG. 2, there is shown slidable upper housing 20 which is essentially an oblong cylinder with a top segment 29a and a bottom segment 29b. The top segment 29a is tapered or rounded at its end and forms push button 22. Positioned below the top segment 29a is a collar 30 which defines an undercut area 32 (FIG. 2B) which serves to hold accordion-pleated flexible plastic sleeve 24 in place. Extending below collar 30 and radially inwardly offset there from is the bottom segment 29b. On the end of surface 34 of the bottom segment are a plurality of evenly spaced fingers 36 which form grooves 38 (FIG. 2A) there between and serve to prevent housing 20 from being disconnected from device 10. Generally, the number of fingers 36 will vary with about four being preferred. Fingers 36 surround and form an annulus about central aperture 39 which permits plunger 40 and center shaft 60 to extend there through.

Plunger 40 is depicted in FIG. 3 in cross section. The plunger 40 is an elongate cylinder having an outer surface 42. The plunger 40 has a shoulder 44 which extends radially outward to form rim 48. On the outer surface 42 of the plunger 40 are equally spaced splines 46. Splines 46 matingly engage grooves 38 of the housing 20 so as to provide alignment of these two parts or components of the dispensing device and to prevent excessive rotation of the pleated sleeve.

In FIG. 4 there is shown an elongated center toothed shaft 60. Shaft 60 is provided within the upper portion 12 of dispensing device 10. Shaft 60 is essentially cylindrical and extends along a major length of upper portion 12 and is provided with an array of teeth 62 which are evenly spaced longitudinally along the shaft 60 such as at a distance of about 0.45 mm. However, it is to be understood that the distance between the teeth can be fixed at any other length and such a distance constitutes the advancement of the shaft with each push on push button 22 as more fully described herein below. Shaft 60 terminates at its lower end in projection 66 which engages piston head 70. Teeth 62 are generally pitched at an angle to facilitate forward shaft advancement and retard backward motion.

Piston head 70, as depicted in FIG. 5, is constituted by a cylindrical wall 72 having at its front and back two external peripheral lips 73a, 73b which form piston aperture 74 therein. Piston head 70 has a central recess 76 which matingly receives shaft projection 66 so that piston head 70 moves in unison with the shaft 60 as an assembly.

Substance reservoir 14 is formed by a portion of outer cylinder 18 and slidably receives piston head 70.

In lower portion 16 of the dispensing device 10, there is provided, as shown in FIG. 6, an applicator 90 for application of the substance. Applicator housing 91 can generally have any desired shape with usually a neck down or a progressively narrower portion proceeding from the upper portion of the applicator to the forward tip 93 thereof so as to dispense the substance contained in reservoir 14 in a small amount and/or area. Alternatively, the applicator 90 is provided at its tip 93 with a plurality of openings or orifices 95 for ejection of the substance. Numerous other configurations of the tip 93 or applicator opening can exist so that the substance can be applied in any desired shape or configuration. Moreover, the applicator tip 93 can be in the form of a brush or a sponge.

A means for advancement of the center toothed shaft 60 so as to drive the piston head 70 is depicted, generally, in FIG. 1. The internal mechanism with regard to the advancement of shaft 60 can generally be any structure known to the art and to the literature such as that described in U.S. Pat. No. 2,771,858 to Cribbs which is hereby fully incorporated by reference. To dispense a predetermined quantity of a substance contained in center reservoir 14, finger or other pressure is applied to slidable push button 22 which compresses accordion-pleated sleeve 24. Upper housing 20 slidably engages plunger 40 after an initial free play or longitudinal travel length, such as about 0.25 inches, defined by the distance between upper housing shoulder 27 and plunger upper end or terminal surface 41. Thus, in a normal position as shown in FIG. 1, upper housing 20 exists in a retracted or rest state wherein a free play distance exists between housing shoulder 27 and the upper end of plunger 40. Upon pressing push button 22, the free play distance is gradually shortened until housing shoulder 27 contacts top surface 41 of plunger 40 where upon the plunger commences to move downwardly in unison with push button 22. The plunger movement distance is controlled by the distance between plunger rim 48 and internal flange 86 which is connected to or integral with the central housing of the dispensing device. This distance is generally set approximately the length of one tooth of central shaft 60, such as about 0.02 inch.

Dispensing of a substance in reservoir 14 through applicator 90 thus occurs in the following manner. Push button 22 is depressed whereby housing 20 will travel downwardly until shoulder 27 contacts plunger 40 which through ratchet drive spring 80 (FIG. 1) engages shaft 60 to produce a longitudinal forward movement of the shaft and thus drive piston head 70 into center reservoir 14 to discharge a substance through applicator 90. The forward advancement of shaft 60 continues until, as noted above, plunger rim 48 contacts internal flange 86 which is usually a distance of one shaft tooth. Upon release of push button 22, compression spring 82 retracts plunger 40 whereas housing spring 25 retracts housing 20, but the toothed center shaft 60 is held by ratchet holding spring 84 (FIG. 1) so as to retain the shaft in its advanced position. Spring 84 is connected to the dispensing device housing so that it does not advance or retract.

As apparent from the above description, push button 22 is free of any contact with the top end of shaft 60. In other words, upon depression of push button 22, it does not contact the top end of shaft 60 but rather housing 20 through shoulder 27 subsequently contacts plunger 40 which advances the same. Thus, push button 22 is free of direct contact with the upper end of central shaft 60 but encloses the same so that it is not exposed. Another advantage of the present invention is that the dispensing device 10 dispenses substance without any rotary action of the upper portion 12 of the dispensing device 10 which would otherwise require two hands to operate the same. Dispensing device 10 is also free of any wheel type engagement with center shaft 60 which normally requires an exact rotation of the wheel to apply a desired amount of substance to an object such as a human body. Rather, push button 22 need only be depressed a desired number of times to apply a suitable amount of substance.

The dispensing device 10 of the present invention has application in various cosmetic, personal care and medicinal applications wherein the substance is desirable a flowable liquid, a semi-solid or a solid such as a powder.

Examples of cosmetic applications include foundation make-ups, blush, lotions, astringents, toners, emollients, lip sticks, eyeliners, brow liners, nail polish and polish removers, under eye covers, mascaras, eye shadows, and the like.

Examples of various personal care items include shampoos such as 2-in-1 shampoos, baby shampoos, conditioning shampoos, bodifying shampoos, temporary hair color shampoos, 3-in-1 shampoos, anti-dandruff shampoos, and hair color maintenance shampoos; skin cleansers including anti-bacterial washes, moisturizing washes, bath and shower gels, facial and foot scrubs; creams and lotions, including skin whiteners, self tanning lotions, sunscreen lotions, barrier lotions, moisturizers, hair styling creams, Vitamin C creams, liquid talc products and antibacterial lotions, shaving preparations, and other moisturizing lotions and creams; skin and hair gels, for example facial masks, body masks, hydroalcoholic gels; hair gels; body gels, sunscreen gels, and the like, as well as other personal care applications such as permanent hair color, toothpaste and the like.

Examples of medicinal applications include topical formulations in the form of creams, lotions, ointments, or gels including antibacterials, antifungals, anesthetics, analgesics, antiseptics/disinfectants, and the like.

While in accordance with the patent statutes the best mode and preferred embodiment have been set forth, the scope of the invention is not limited thereto, but rather by the scope of the attached claims.

What I claim is:

1. A dispensing device comprising:
    an upper portion having a housing;
    a center substance reservoir portion connected to said upper portion; and
    a lower cap portion connected to the center portion and containing an applicator;
    wherein an inner surface of said upper portion housing is capable of contacting a plunger, said plunger operatively providing forward movement to a center toothed shaft, thereby driving a piston head in order to dispense a substance from said applicator; wherein the plunger includes a hollow cylindrical portion and wherein the center toothed shaft extends through at least a portion of the hollow plunger.

2. A dispensing device according to claim 1, wherein said upper portion housing comprises a top segment and a bottom segment, said top segment tapering at an end to form a push button.

3. A dispensing device according to claim 2, wherein said upper portion housing and said plunger are slidable in a forward longitudinal direction, wherein a first spring is operatively connected between the upper housing portion and an outer cylinder, wherein the first spring maintains the upper portion housing a distance away from an end of the plunger in a non-depressed condition, and wherein a second spring is operatively connected between the outer cylinder and the plunger which maintains the plunger a distance away from an internal flange of the outer cylinder when the upper portion housing is in the non-depressed condition.

4. A dispensing device according to claim 3, wherein said substance to be dispensed is a cosmetic substance, a personal care substance or a medicinal substance.

5. A dispensing device according to claim 2, wherein said upper portion housing further includes an accordion-pleated flexible plastic sleeve portion, said sleeve portion held in place by a collar defining an undercut area.

6. A dispensing device according to claim 5, wherein said accordion pleated sleeve portion is made from one or more of silicone rubber, polypropylene, low density polyethylene, ultra-low density polyethylene, or polybutylene.

7. A dispensing device according to claim 2, said bottom segment having a surface including a plurality of evenly-spaced fingers forming grooves there between, said fingers forming an annulus about a central aperture such that said plunger and said center shaft extend there through.

8. A dispensing device according to claim 7, wherein said plunger includes a shoulder having a rim, and wherein the shoulder rim contacts an internal flange of an outer cylinder in a depressed condition.

9. A dispensing device according to claim 8, wherein said substance to be dispensed is a cosmetic substance, a personal care substance or a medicinal substance.

10. A dispensing device according to claim 8, wherein an outer surface of said plunger has equally-spaced splines which matingly engage with said grooves of said upper housing.

11. A dispensing device according to claim 10, wherein said upper portion housing slidably engages said plunger for a limited distance before contact there between whereby said plunger and said housing operate in unison as through a housing shoulder.

12. A dispensing device according to claim 1, wherein said center-toothed shaft is an essentially cylindrical, elongate shaft having an array of evenly-spaced teeth extending longitudinally along said shaft and a shaft projection at a lower end of said shaft.

13. A dispensing device according to claim 12, wherein said substance to be dispensed is a cosmetic substance, a personal care substance or a medicinal substance.

14. A dispensing device according to claim 12, wherein said teeth of said shaft are spaced apart from each other at a distance of about 0.45 mm.

15. A dispensing device according to claim 12, wherein a first spring is operatively connected between the upper housing portion and an outer cylinder, wherein the first spring maintains the upper portion housing a distance away from an end of the plunger in a non-depressed condition, and wherein a second spring is operatively connected between the outer cylinder and the plunger which maintains the plunger a distance away from an internal flange of the outer cylinder when the upper portion housing is in the non-depressed condition.

16. A dispensing device according to claim 15, wherein said substance to be dispensed is a cosmetic substance, a personal care substance or a medicinal substance.

17. A dispensing device according to claim 12, wherein said piston head comprises a cylindrical wall having front and back peripheral lips.

18. A dispensing device according to claim 17, wherein a central recess of said piston head matingly receives said shaft projection such that said piston head moves in unison with said shaft.

19. A dispensing device according to claim 1, wherein said upper portion housing, said center reservoir portion and said lower cap portion are made from one or more of polybutylene, polyester, polyethylene, ethylene-ethyl acrylate, ethylene-vinyl acetate, or polypropylene.

20. A dispensing device according to claim 1, wherein said applicator includes a brush or a sponge.

21. A dispensing device according to claim 1, wherein said substance to be dispensed is a cosmetic substance, a personal care substance or a medicinal substance.

22. A dispensing device according to claim 1, wherein said device is operable without rotary action of said upper portion.

23. A dispensing device, comprising:
a slidable upper housing, an internal shaft, a substance reservoir, and an applicator;
said upper housing operatively connected to said shaft other than at an end portion of the shaft, said shaft having a second end connected to a piston head located in said substance reservoir so that upon pressing said slidable upper housing said piston is capable of supplying a substance through said applicator connected to said reservoir, wherein a first spring is operatively connected between the upper housing and an outer cylinder, wherein the first spring maintains the upper housing a distance away from an end of a plunger in a non-depressed condition, and wherein a second spring is operatively connected between the outer cylinder and the plunger which maintains the plunger a distance away from an internal flange of the outer cylinder when the upper housing is in the non-depressed condition.

24. A dispensing device according to claim 23, wherein said upper housing has a push button portion located at the upper extremity thereof and wherein said push button portion upon depression thereof is not capable of contacting said shaft top portion.

25. A dispensing device according to claim 24, wherein said slidable upper housing is capable of being slidably moveable in a forward longitudinal direction with respect to said plunger a distance until contact there between where upon said housing and said plunger move in unison.

26. A dispensing device according to claim 25, wherein said substance to be dispensed is a cosmetic substance or a medicinal substance or a personal care substance.

27. A dispensing device according to claim 25, wherein said dispensing device has an outer cylinder, wherein said upper housing has a flexible pleated sleeve contacting said outer cylinder and wherein said flexible sleeve is capable of expanding and retracting.

28. A dispensing device according to claim 27, wherein said applicator has a tip portion and wherein said tip portion contains a plurality of orifices therein.

29. A dispensing device according to claim 27, wherein said shaft is capable of advancing in a forward longitudinal direction.

30. A dispensing device according to claim 29, wherein said substance to be dispensed is a cosmetic substance or a medicinal substance or a personal care substance, wherein the plunger includes a hollow cylindrical portion and wherein the center toothed shaft extends through at least a portion of the hollow plunger.

31. A dispensing device according to claim 29, wherein said piston head is slidably received in said substance reservoir.

32. A dispensing device according to claim 31, wherein said outer cylinder forms a portion of said substance reservoir.

33. A dispensing device according to claim 32, wherein said upper housing is made of polypropylene.

34. A dispensing device according to claim 23, wherein said upper housing is made of plastic, wherein the plunger includes a cylindrical portion which is hollow and wherein the center toothed shaft extends through at least a portion of the plunger.

35. A dispensing device according to claim 34, wherein said applicator has a tip portion and wherein said tip portion contains a plurality of orifices therein.

36. A dispensing device according to claim 23, wherein said applicator has a tip portion and wherein said tip portion contains a plurality of orifices therein.

37. A dispensing device according to claim 36, wherein said substance to be dispensed is a cosmetic substance or a medicinal substance or a personal care substance.

38. A dispensing device according to claim 23, wherein said substance to be dispensed is a cosmetic substance or a medicinal substance or a personal care substance, wherein the plunger includes a hollow cylindrical portion and wherein the center toothed shaft extends through at least a portion of the hollow plunger.

* * * * *